(12) United States Patent
Lacy

(10) Patent No.: US 11,717,468 B2
(45) Date of Patent: *Aug. 8, 2023

(54) SYSTEM FOR GASTROINTESTINAL ENGINEERING TO RESTORE NORMAL YOUTHFUL BODILY FUNCTIONS

(71) Applicant: Franklin R. Lacy, Marco Island, WA (US)

(72) Inventor: Franklin R. Lacy, Marco Island, WA (US)

( * ) Notice: Subject to any disclaimer, the term of this patent is extended or adjusted under 35 U.S.C. 154(b) by 481 days.

This patent is subject to a terminal disclaimer.

(21) Appl. No.: 16/896,667

(22) Filed: Jun. 9, 2020

(65) Prior Publication Data

US 2020/0297576 A1 Sep. 24, 2020

Related U.S. Application Data

(63) Continuation of application No. 14/862,533, filed on Sep. 23, 2015, now Pat. No. 10,709,636, and a continuation of application No. 13/206,252, filed on Aug. 9, 2011, now Pat. No. 9,155,677.

(51) Int. Cl.
| | | |
|---|---|---|
| *A61H 21/00* | (2006.01) | |
| *A61H 23/00* | (2006.01) | |
| *A61H 23/02* | (2006.01) | |
| *A61B 17/00* | (2006.01) | |
| *A61H 11/00* | (2006.01) | |

(52) U.S. Cl.
CPC ............. *A61H 21/00* (2013.01); *A61H 23/02* (2013.01); *A61B 17/00234* (2013.01); *A61B 2017/00734* (2013.01); *A61H 11/00* (2013.01); *A61H 2201/0111* (2013.01); *A61H 2201/0153* (2013.01); *A61H 2201/0157* (2013.01); *A61H 2201/0192* (2013.01); *A61H 2201/1284* (2013.01); *A61H 2201/163* (2013.01); *A61H 2201/165* (2013.01); *A61H 2201/169* (2013.01); *A61H 2201/1645* (2013.01); *A61H 2205/086* (2013.01); *A61H 2205/087* (2013.01)

(58) Field of Classification Search
CPC ......... A61H 21/00; A61H 23/00; A61H 23/02
See application file for complete search history.

(56) References Cited

U.S. PATENT DOCUMENTS

| | | | | |
|---|---|---|---|---|
| 750,735 | A * | 1/1904 | Turke | A61K 41/0047 604/20 |
| 5,419,334 | A * | 5/1995 | Miyagawa | A61B 8/4461 600/463 |
| 6,681,783 | B2 * | 1/2004 | Kawazoe | A61B 1/122 134/169 C |
| 6,984,205 | B2 * | 1/2006 | Gazdzinski | A61B 5/4255 600/407 |
| 8,690,818 | B2 * | 4/2014 | Bennett | A61K 41/0047 604/20 |

(Continued)

*Primary Examiner* — Michael J Tsai
(74) *Attorney, Agent, or Firm* — Clark A. Puntigam; Jensen & Puntigam P.S

(57) ABSTRACT

This is to improve performance of selected internal organs by stimulating the organs through vibration and vibrating action to restore their normal useful functions by vibrating action. The system includes a probe which is introduced through the rectum and has a vibrating element at the end of a flexible shaft having a length sufficient to reach the ileosecal valve in the intestinal tract.

4 Claims, 4 Drawing Sheets

(56) References Cited

U.S. PATENT DOCUMENTS

| | | | | |
|---|---|---|---|---|
| 2003/0208223 A1* | 11/2003 | Kleiner | .............. | A61B 17/3431 |
| | | | | 606/198 |
| 2007/0238940 A1* | 10/2007 | Amirana | .............. | A61B 5/4839 |
| | | | | 600/302 |
| 2008/0154160 A1* | 6/2008 | Noriega | ................ | A61H 21/00 |
| | | | | 601/46 |
| 2010/0045289 A1* | 2/2010 | Chopra | ............ | G01R 33/56358 |
| | | | | 324/307 |
| 2014/0330068 A1* | 11/2014 | Partsch | ................... | A61N 7/00 |
| | | | | 607/101 |
| 2015/0196454 A1* | 7/2015 | Levy | ...................... | A61H 19/32 |
| | | | | 600/38 |

* cited by examiner

SYSTEM FOR GASTROINTESTINAL ENGINEERING TO RESTORE NORMAL YOUTHFUL BODILY FUNCTIONS

PRIOR APPLICATIONS (PRIORITY)

This application is a continuing application of pending application Ser. No. 14/862,533, filed on Sep. 23, 2015, which was a continuing application of application Ser. No. 13/062,252, filed on Aug. 9, 2011, now abandoned.

TECHNICAL FIELD

This invention relates generally to methods and apparatus for treatment of gastrointestinal atrophy, also referred to as gastrointestinal engineering and/or vascular engineering herein, and more specifically concerns a system for restoring normal/youthful bodily functions including urination, metabolism, bowel movement, sex drive, weight control and esophagus function.

BACKGROUND OF THE INVENTION

There is widespread recognition of the effects of aging. Bodily functions slow down and sometimes body parts malfunction. In the gastrointestinal system, food moves down the esophagus through the esophageal sphincter muscle into the stomach and from there enters the first parts of the small intestine, e.g. the duodenum and the jejunum, then through the final portion of the small intestine, called the ileum; and then through the colon. The unabsorbed remaining portion of the food is evacuated through the rectum.

During this process, nourishment is absorbed into the blood stream, which in turn is cleansed of liquid waste by the kidneys with the resulting release of urine into the bladder for evacuation through the urethra. The pancreas, which is located below the stomach, introduces stomach-acid-neutralizing bicarbonate, insulin, etc. into the duodenum. A series of mostly involuntary nerve sensors control this process. This includes the control of both band-like and longitudinal muscular action to produce movement of solids through the intestines. This function is much like an earth worm's method of propulsion. Villi lining the intestines pick up nutrients, liquids, and enzymes for movement into the vascular system. In the vascular system, however, blood vessels can also lose their flexibility and size with age, with resulting decrease in bodily function.

Urine release is controlled by the urethral sphincter muscles, which often become weak with age, causing urine leakage, and incontinence. Sleep is interrupted by frequent trips to the bathroom, along with a daytime need for wearing adult diapers or an external reservoir. Medications may help, but they have possible side effects and often produce only short term results because of bodily acclimation.

Fecal matter release is controlled by the anal sphincter muscles, which can become weak with age, resulting in at least some degree of fecal incontinence.

The esophageal sphincter at the cardiac end of the stomach controls prevention of stomach acid backing up into the esophagus, which would otherwise cause lesions and "heart burn" or worse. This sphincter often becomes weak and stays open with age. Also, the esophagus gets narrower with age making it sometimes difficult for food to readily pass through it.

Further, as the body ages, processed food typically moves more slowly through the intestines and stays in the gastro- intestinal system longer. The result is greater absorption of nutrients from the same quantity of food and deterioration of the quality of the food moving through the gastrointestinal tract. This results in greater weight gain for the same amount of food eaten, possible flatulence, and possible other intestinal maladies that can be absorbed and passed on to the vascular system for delivery throughout the body. This could be a source of disease and malfunction of many organs, including the heart, the brain, the skin, the eyes, and the lungs.

DISCLOSURE OF THE INVENTION

Accordingly, the system for reversing atrophy of the function of the gastrointestinal tract comprises a colon probe adapted for insertion into the gastrointestinal tract in the human body by insertion of the probe into the rectum, the colon probe having a flexible shaft with a vibrating tip at a distal end thereof, which vibrates when it is activated by a vibration system at a selected frequency and amplitude of 20-50 Hz and 0.02-0.13 inches, wherein the vibrations of the vibrating tip directly stimulate the nerve endings or the nerve endings and muscles along the gastrointestinal tract, wherein the flexible shaft includes a handle at a proximal end thereof, wherein the flexible shaft is configured such that the vibrating tip can extend through the colon to the ileocecal valve, with the handle remaining outside of the body, and wherein the vibrating tip is bulbous in the form of a bulb, precluding inflation, and has a diameter such that it can extend into the rectum and then into the gastrointestinal tract and such that it is greater than a urethra diameter.

BEST MODE FOR CARRYING OUT THE INVENTION

Figure 1:
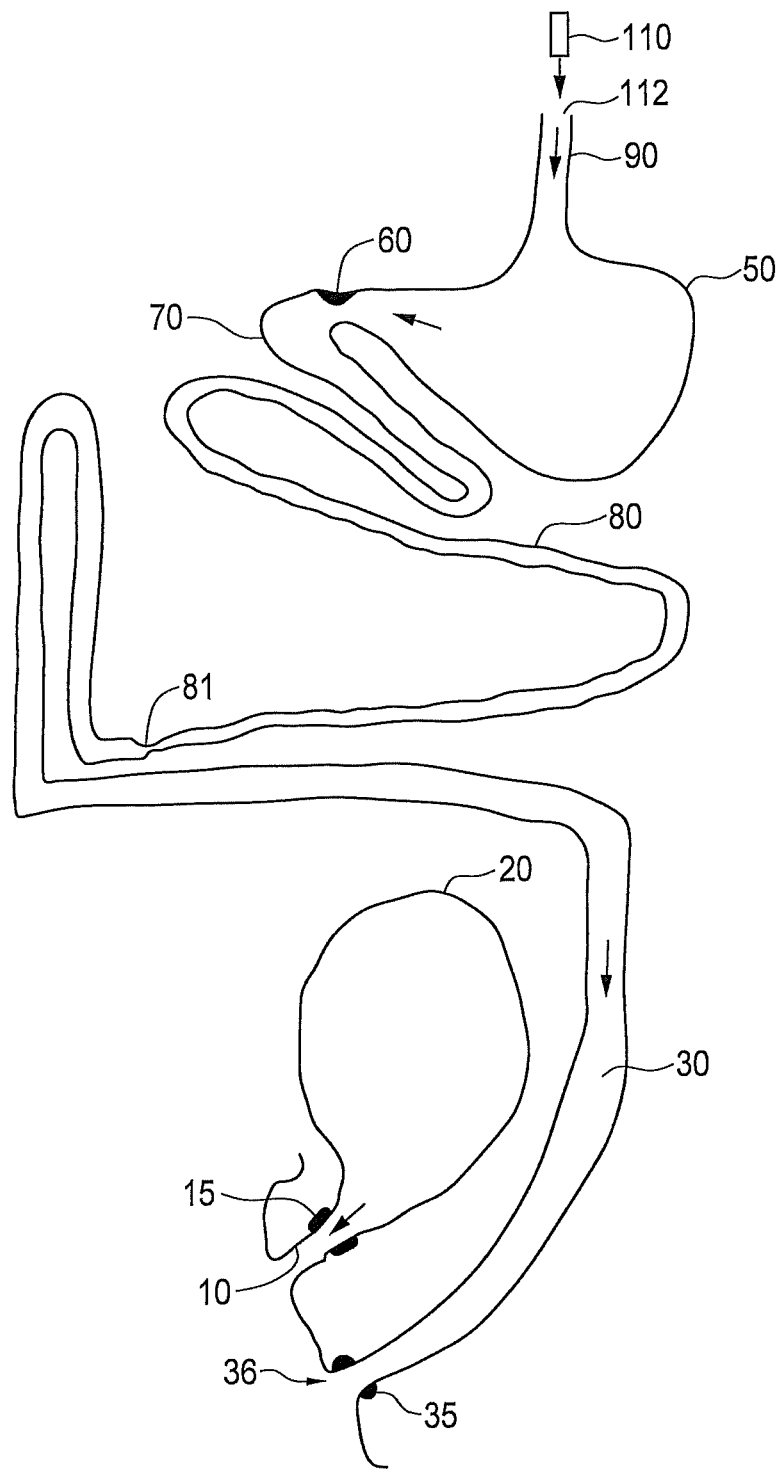
FIGS. 1 and 1A show a schematic view of one embodiment of the present system described herein and its operation in the gastrointestinal system.

Referring now to the FIG. 1, a lower internal abdominal body region is shown representationally, but without some internal organs, including those unique to the respective sexes. The urethra (10) carries urine from the bladder (20). The urethral sphincter muscles (15) control the evacuation of urine. In one aspect of the present system, a vibrating capsule 110 is swallowed (at 112) and passes through the digestive system in normal course. The capsule is the size of a 1 gram pill, approximately 8 mm (5/16 inch) in diameter and 19 mm (3/4 inch) long. Other sizes can also work well. The capsule has an internal mechanism, such as a motor or oscillating field, which causes it to vibrate. The frequency of vibration can vary. Preferably it is in the range of 10-50 Hz. The amplitude of vibration is approximately 0.03-0.13 inches. The capsule can be made of various materials, including high impact plastic. The rapid vibration of the capsule internally challenges/stimulates nerve endings along the digestive tract, causing them in effect to come to life with improved capability. The rapid vibration of the capsule also internally challenges/stimulates the muscles and the vascular system in the intestinal wall, causing them to come to life with improved capability as well. The movement of food through the small intestine and colon is expedited after treatment when the capsule's function is completed.

Time delay or remote triggering activation of the above device can provide activation/treatment of the whole small intestine, a section at a time. An alternative treatment described in more detail below is to use a deep tissue multiple station vibrator positioned under pressure against the surface of the skin covering the area of the small intestine. It is used for 15 minutes of constant vibration under pressure to cover every square inch of small intestine using the same 10-50 Hz, 0.03-0.12 inch amplitude vibration described above. This will stimulate the intestinal nerves, the muscles in the intestinal wall, and the surrounding vascular system to expedite the movement of food through the small intestine and colon.

Referring still to FIG. 1, the vibrating capsule passes through esophagus 90 into stomach 50. It then passes into the pyloric opening, past the pyloric sphincter 60, and then through the duodenum 70, at which point it begins passage through the remainder of the small intestine 80. At the ileocecal valve 81 the vibrating capsule enters the colon 30, where it ultimately passes through the rectum 36 and is evacuated via the anal sphincter 35.

Figure 4:
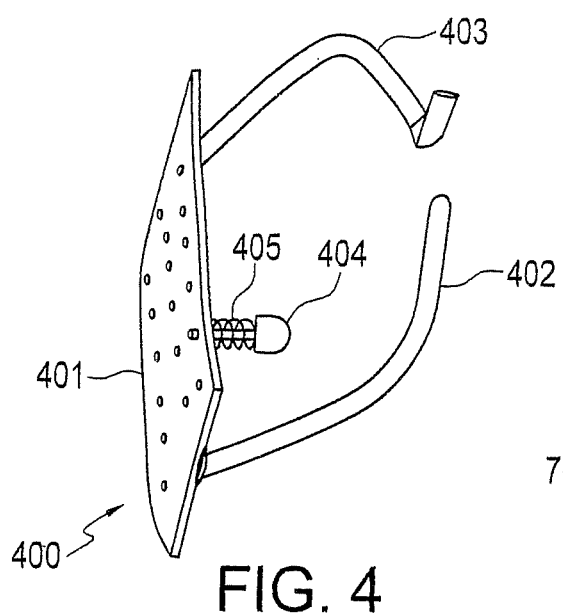
FIG. 4 is a schematic view of an external applicator embodiment.

In the alternate treatment version 400 (FIG. 4) a plate 401 approximately 4 inches by 8 inches with a grid of deep tissue vibrating fingers 404 is applied under pressure against the skin to vibrate every square inch of the small intestines for 15 minutes. This plate can either be strapped by belt 402, 403 onto the lower abdomen opposite the small intestine, or the user can lay on it in order to maintain abdominal pressure during the vibration treatment. The plate can be curved to match the contour of the body in the area of the small intestine. Each finger vibrator is mounted with a spring 405 in order to maintain force of pressure on the abdomen.

Figure 7:
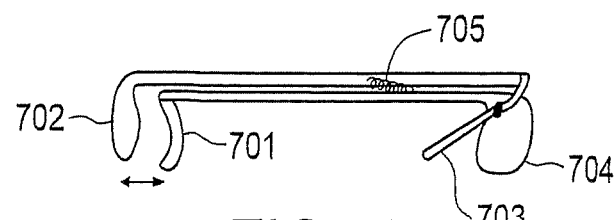
FIG. 7 is a schematic view of yet another applicator.

In another alternate configuration where hard to reach organs need to be treated, item 700 (FIG. 7) includes an opposing long clamp that works much like a fish hook extractor. In the configuration shown, opposing jaws 701, 702 are released by compressing a lever-type arm at one end of the handle 704. One of the jaws 702 on the other end of the tool has a vibrator while the other jaw has a clamping pad. Spring 705 and hinge release 703 are included in the embodiment. A small incision might be needed, providing access of the tool to the organ or vessel to be treated.

Another embodiment of the above system, also shown in FIG. 1, includes a vibrating colon probe 200 (FIG. 1A) which has a tip 202 which enters colon 30 by passing through the rectum 36. The colon probe 200 has a vibrating tip or bulb 202 at one end, a long flexible shaft 203, possibly containing electric power supply wires and/or cables, and a handle 201 at the other end. Power can also be supplied by batteries on a self-contained basis. The handle 201 can contain controls and a power source for the tip 202. The shaft 203 and tip 202 have an approximate working length up to 168 mm (66 inches) in order for the colon probe tip to possibly reach the ileocecal valve 81. The diameter of the flexible shaft 203 is approximately 1 cm (⅜ inch). In the embodiment shown, tip 202 is bulbous, although other shapes, such as a football shape, can be used. It can have a soft, rubbery coating. It has an approximate diameter of 15.9 mm (0.625 inch) and an approximate length of 4.6 cm (2 inches) in the embodiment shown.

Figure 5:
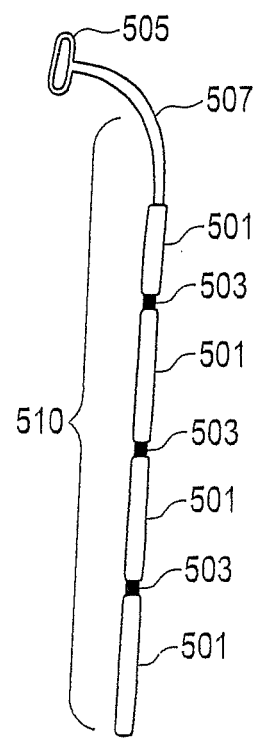
FIG. 5 is a schematic view of a multiple applicator embodiment.

A series of similar probe tips 501-501 can be joined in tandem to form an applicator 500 to simultaneously treat the whole length of the colon, as shown in FIG. 5. In the tandem configuration each joined tip/vibrator member can be independently vibrated. In that configuration an elastic knot-like connection 503-503 can be used to join each vibrator member in tandem (sausage style). The knots allow independent vibration of each vibrator member without interference of amplitude from adjacent vibrator members. The applicator also includes a handle 505 and an insertion/removal strap 507.

Figure 3:
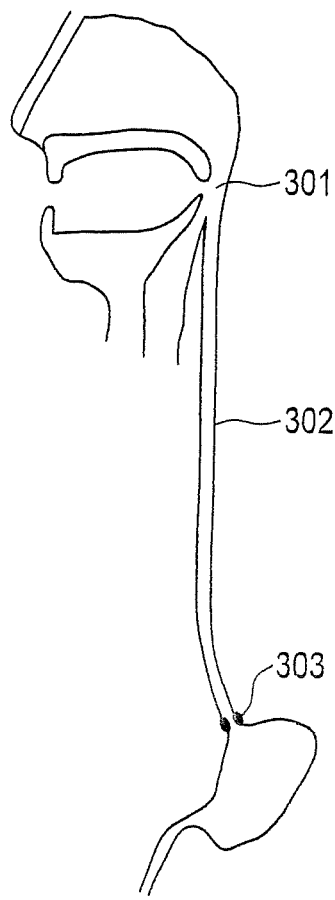
FIG. 3 is a schematic view of one portion of the present system.

Other lengths and diameters of probe tips 202 can be used. There may be a plurality of vibrating elements positioned along the length of the probe, similar to that discussed above, individually controllable or controllable as a group. With this arrangement, the entire length of the large intestine can be treated at once. This arrangement is equally applicable for treating of the esophagus, as shown (without the treatment device) in FIG. 3 with the pharynx shown at 301, the esophagus at 302 and the esophageal sphincter at 303.

In operation, sufficient time must be allowed while the colon probe 200 is pushed and pulled along the colon walls in order to challenge (treat) the nerve endings and exercise the wall muscles and vascular system in and around the colon so as to restore their youthful function. Because the time of treatment can take up to 15 minutes in each position being treated, an alternative approach is to ingest or implant a tip 202. The tip 202 will be free of the shaft and self-contained after it is internally inserted. The tip 202 would continue to vibrate under its own self-contained power. It will travel along the colon while vibrating until it is evacuated through the rectum via a bowel movement.

Another alternative is to implant a vibrating tip in the colon with attached sealed wires extending to a point outside the body to provide power. In this case, the patient would remain at a medical facility until the treatment is complete. Item 200 or item 500 can be used in the esophagus with a vibration length up to 9 inches. The small push/pull cord or plastic strip at the mouth end facilitates insertion and removal and breathing during the procedure. Although the length of treatment at each position is approximately 15 minutes, this could vary. It would typically be used for treating the esophagus and the esophageal valve (where the esophagus joins onto the cardiac side of the stomach).

Figure 1A:
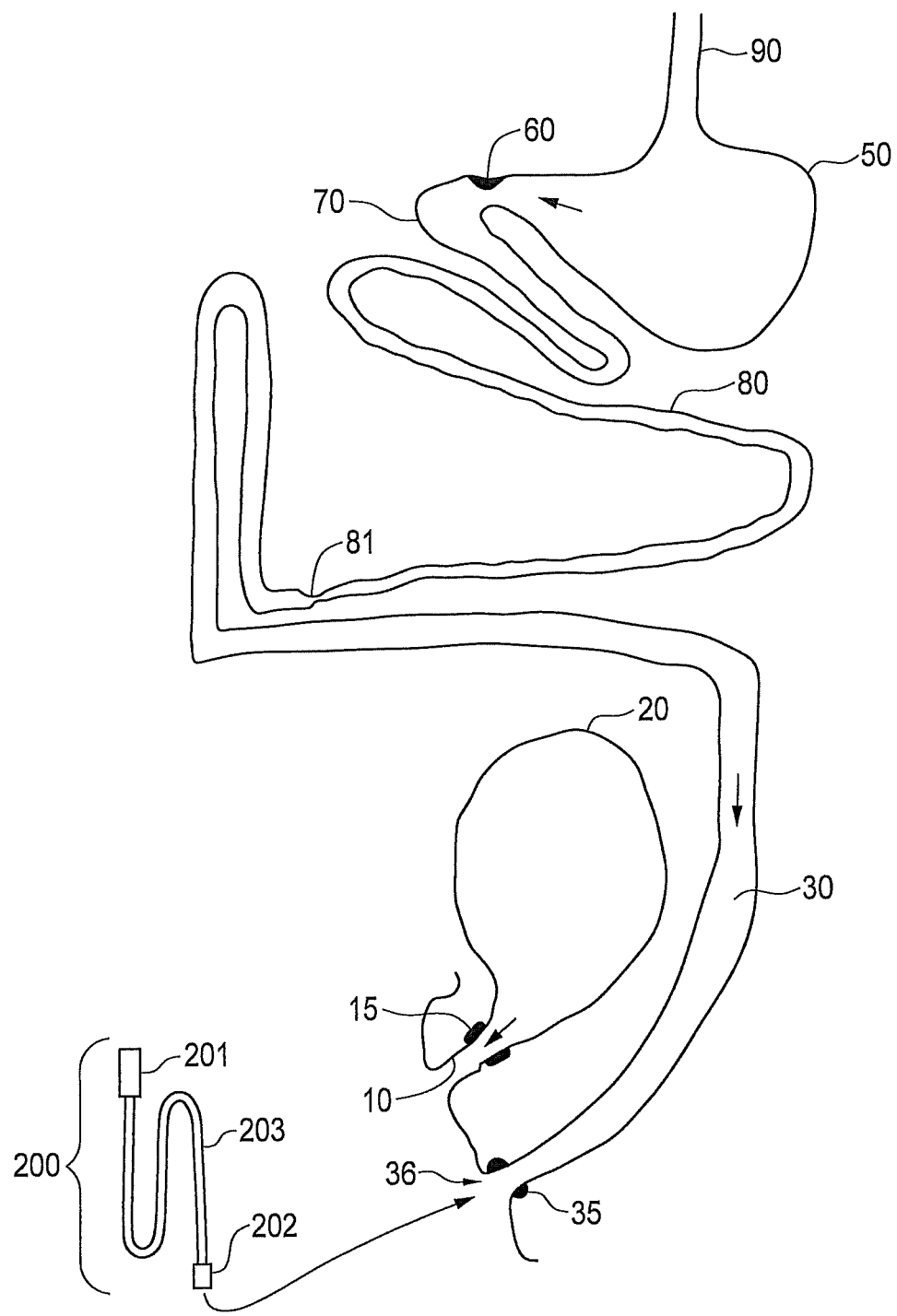
Figure 2:
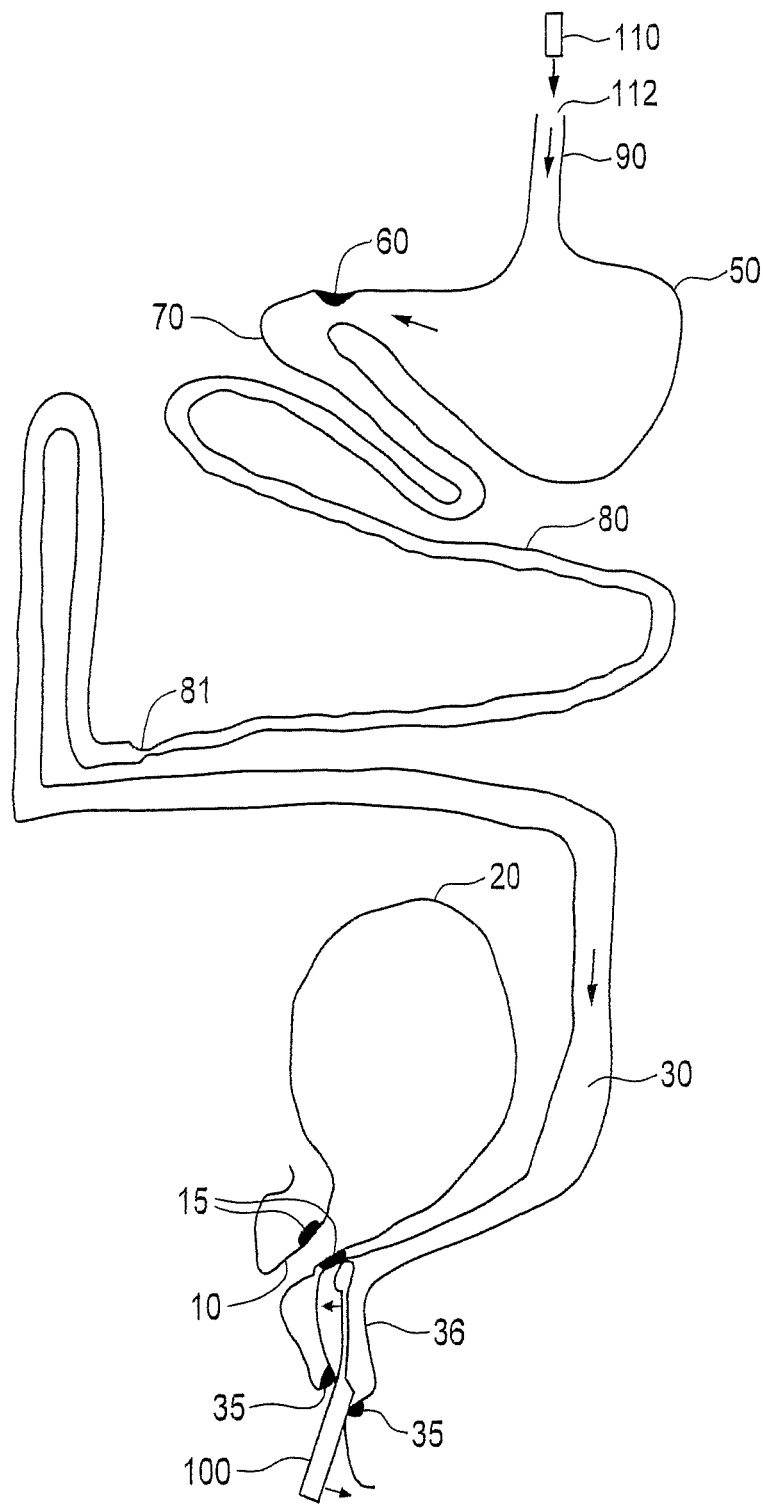
FIG. 2 is a schematic view showing another embodiment of the present system.
Figure 6:
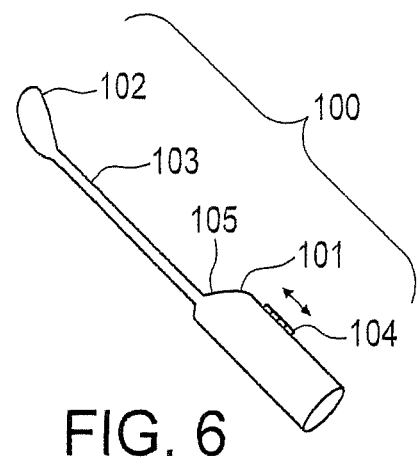
FIG. 6 is a schematic view of another applicator.

Referring now to FIG. 2, a lower abdominal body region is again shown representationally, although some organs, including those unique to each sex, are not included. A shorter version of the colon probe 200 of FIG. 1A is used to vibrate rapidly (for example 10-50 Hz) and thus challenge/stimulate the nerve ends and exercise the urethral sphincter muscles 15, which control urination. It can also through vibration separately challenge/stimulate the nerve ends and muscles in the rectum and colon and exercise the anal sphincter muscle 35, which controls bowel movements. This instrument is hereinafter referred to as a sphincter probe 100. The sphincter probe is shown in more detail in FIG. 6. It includes a tip 102, which is positioned in the rectum area 36 and applies forward and downward pressure against the urethral sphincters 15 when positioned as shown in FIG. 2.

The sphincter probe 100 has a vibrating tip 102 at one end, a flexible shaft 103 possibly containing electric power supply wires, and a handle 101 with, in some cases, dual slider switches 104 at the other end. An area 105 at the top of the handle is a second vibrator member, used to stimulate the anal sphincter. The handle 101 contains two controls, one each for the two sources of vibration; alternatively, one switch can control both vibrations. The handle also contains a source of power for the separate vibrations at the tip 102 and the handle area 105 for anal sphincter 35 independent treatment. The shaft 103 and tip 102 have an approximate working length up to 15.2 mm (6 inches) in order for the sphincter probe 100 to possibly simultaneously rapidly vibrate both the urethral sphincter 15 and the anal sphincter 35. These two vibrating parts can be used for treating both urinary incontinence and fecal incontinence, simultaneously if desired. The diameter of the flexible shaft 103 is approximately 1 cm (⅜ inch), but it could be as large as 2.5 cm (1 inch) and could also vibrate. The tip 102 is bulbous, although other shapes can be used. It can have a soft, rubbery coating. The approximate diameter of the tip is 2.5 cm (1 inch) and its length is approximately 4.6 cm (2 inches). Other lengths and diameters of tip 102 can be used.

Sufficient time must be allowed for treatment as the tip 102 of the sphincter probe 100 pushes against the urethral sphincter 15 during the vibration action of the tip and/or the handle area 105 pushes against the anal sphincter 35 in order to challenge/stimulate the nerve endings and muscles of these sphincters and restore their youthful function. Typically, it takes up to 15 minutes for treatment to be effective. Sitting on the probe at an angle provides good results, relative to urinary incontinence and/or having to get up at night to relieve urinary pressure.

In addition to the above, article 100 (not 101) with the tip 102 approximately 2 inches along the shaft 103 may be applied outside the body against the perineum and pushed forward against the perineum and urethral sphincter as well as the fine vessels in the scrotum leading to the testes. This can best be achieved by sitting on item 100 while it is vibrating to achieve enough forward and upward pressure. The results achieved will be exercising the muscles and charging the nerve endings that control the urethral sphincter, as well as making the tiny blood vessels leading to the testes better able to provide blood flow for improved sexual activity. The later will take a week after treatment for improved results including morning erections upon waking when formerly there were none.

What is claimed is:

1. A system for reversing atrophy of the function of the gastrointestinal tract, comprising:
a colon probe adapted for insertion into the gastrointestinal tract in the human body by insertion of the probe into the rectum, the colon probe having a flexible shaft with a vibrating tip at a distal end thereof, which vibrates when it is activated by a vibration system at a selected frequency and amplitude of 20-50 Hz and 0.02-0.13 inches, wherein the vibrations of the vibrating tip directly stimulate the nerve endings or the nerve endings and muscles along the gastrointestinal tract, wherein the flexible shaft includes a handle at a proximal end thereof, wherein the flexible shaft is configured such that the vibrating tip can extend through the colon to the ileocecal valve, with the handle remaining outside of the body, and wherein the vibrating tip is bulbous in the form of a bulb, precluding inflation, and has a diameter such that it can extend into the rectum and then into the gastrointestinal tract and such that it is greater than a urethra diameter.

2. The system of claim 1, wherein the vibration system is contained within the colon probe.

3. The system of claim 1, wherein the vibration system is positioned external to the colon probe but is connected to the vibrating tip.

4. The system of claim 1, wherein the handle permits the user to push and/or pull the colon probe when the colon probe is present in the gastrointestinal tract.

* * * * *